United States Patent [19]

Ramirez et al.

[11] Patent Number: 4,654,213

[45] Date of Patent: Mar. 31, 1987

[54] NOVEL ANTI-MICROBIAL SYSTEMS CONTAINING THE MAGNESIUM SULFATE ADDUCT OF 2,2'-DITHIOBIS-PYRIDINE-1,1'-DIOXIDE AND A WATER SOLUBLE ZINC SALT

[75] Inventors: José E. Ramirez, Trumbull; Robert J. Tanko, Cheshire; Mohan Vishnupad, Monroe; William H. Schmitt, Branford, all of Conn.

[73] Assignee: Cheesebrough-Pond's Inc., Greenwich, Conn.

[21] Appl. No.: 774,725

[22] Filed: Sep. 11, 1985

[51] Int. Cl.$^4$ .................. A61K 31/555; A61K 33/30; A01N 55/02; A01N 59/16
[52] U.S. Cl. ..................................... 424/145; 424/56; 514/188
[58] Field of Search ................ 514/335, 188; 424/145, 424/49, 56

[56] References Cited

U.S. PATENT DOCUMENTS

| | | | |
|---|---|---|---|
| 3,890,434 | 6/1975 | Weisse et al. | 514/335 |
| 4,152,431 | 5/1979 | Klein | 514/335 |
| 4,163,783 | 8/1979 | Klein et al. | 514/335 |
| 4,410,446 | 10/1983 | Cheng et al. | 424/145 |

FOREIGN PATENT DOCUMENTS

| | | | |
|---|---|---|---|
| 54-15939 | 2/1979 | Japan | 514/335 |
| 60-16973 | 1/1985 | Japan | 514/335 |

OTHER PUBLICATIONS

Chem. Abst. 69:34387w (1968)—Okamoto et al.
Chem. Abst. 80:91617x (1974)—Elkhouly et al.
Chem. Abst. 87:161376p (1977)—Wedig et al.
Chem. Abst. 88:177003w (1978)—Wedig et al.
Chem. Abst. 91:32995g (1979)—Gloor et al.
The Merck Index 9th ed-(1976)-pp. 1307-1309-Merck & Co.

Primary Examiner—Douglas W. Robinson
Attorney, Agent, or Firm—Morgan & Finnegan

[57] ABSTRACT

This invention relates to novel antimicrobial systems containing a water-soluble, non-ionic pyrethione derivative known chemically as the magnesium sulfate adduct of 2,2'-dithiobis-pyridine-1,1'-dioxide (referred to hereinafter as "the magnesium sulfate adduct") and a water soluble zinc salt.

The antimicrobial systems of this invention may be incorporated in various useful therapeutic and cleansing compositions such, for example, as surgical scrub compositions, skin disinfectants, mouthwashes, deodorants, hospital cleaners, etc.

5 Claims, No Drawings

NOVEL ANTI-MICROBIAL SYSTEMS CONTAINING THE MAGNESIUM SULFATE ADDUCT OF 2,2'-DITHIOBIS-PYRIDINE-1,1'-DIOXIDE AND A WATER SOLUBLE ZINC SALT

SUMMARY OF INVENTION

This invention relates to novel antimicrobial systems containing a water-soluble, non-ionic pyrethione derivative known chemically as the magnesium sulfate adduct of 2,2'-dithiobis-pyridine-1,1'-dioxide (referred to hereinafter as "the magnesium sulfate adduct") and a water soluble zinc salt. More particularly, it has been found that the presence of a water soluble zinc salt appears to enhance to an unexpected extent the antimicrobial activity of the magnesium sulfate adduct against certain types of microorganisms such, for example, as *Staphylococcus epidermidis*, *Staphylococcus aureus* and *Pseudomonas aeruginosa*.

The antimicrobial system of this invention may be incorporated in various useful therapeutic and cleansing compositions such, for example, as surgical scrub compositions, skin disinfectants, mouthwashes, deodorants, hospital cleaners, etc.

BACKGROUND OF THE INVENTION

The magnesium sulfate adduct used in accordance with this invention is a well known broad spectrum antimicrobial agent. For example, a well known commercially available form is sold by Olin Chemicals of Stanford, Conn. under the trade name "OMADINE MDS" which is the trihydrate form.

While the magnesium sulfate adduct used in this invention has broad spectrum antimicrobial activity, it lacks the desired activity against *Pseudomonas aeruginosa*, the microorganism associated with infection that often follows severe burning of the skin.

Examples of additional microorganisms against which it would be desirable to enhance the antimicrobial activity of the pyrithione derivative used in this invention are *Staphylococcus aureus* and *Staphylococcus epidermidis*.

OBJECTS OF THE INVENTION

An object of the invention is to provide novel antimicrobial systems wherein enhanced antimicrobial activity of the magnesuim sulfate adduct is effectuated against certain types of microorganisms.

Another object of this invention is to provide novel therapeutic and cleansing compositions having incorporated therein the antimicrobial system set forth in the foregoing object.

GENERAL DESCRIPTION OF THE INVENTION

It has been found that the objects of this invention may be realized by forming an antimicrobial system containing the magnesium sulfate adduct and a water soluble salt.

For example, microbiological testing indicates that the activity of magnesium sulfate adduct against *Ps. aeruginosa* is enhanced in the presence of water soluble zinc salts.

The preferred zinc salt used in accordance with this invention is zinc chloride ($ZnCl_2$). Other water soluble zinc salts which may be used are zinc acetate, zinc sulfate, zinc nitrate, zinc phenylsulfonate, etc.

In general, it has been found that in order to obtain the desired enhancement of antimicrobial activity in accordance with the present invention the zinc salt should be in an amount from about 1 to about 10, and preferably from about 1 to 1 parts by weight per part of the magnesium sulfate adduct.

In the therapeutic and/or cleansing composition of this invention the magnesium sulfate adduct in general is in an amount from about 0.1 to 1.5% by weight and the zinc salt from about 0.1 to 1% by weight, of the total composition.

It has been found that a most useful antimicrobial composition that may be obtained utilizing the present invention is a surgical scrub compositions employing the antimicrobial system of this invention in an anhydrous foamable base composition. Such surgical scrub compositions have been found useful in killing both *Staphylococcus aureus* and *Pseudomonas aeruginosa* types of bacteria. The anhydrous foamable base composition contains petroleum jelly, mineral oil and a mild detergent (Sodium cocoyl isethionate).

SPECIFIC DESCRIPTION OF THE PRESENT INVENTION

In order to illustrate the invention by specific examples a number of compositions containing the magnesium sulfate adduct and zinc chloride in accordance with the invention were tested for antimicrobial activity and compared with control compositions containing either the magnesium sulfate adduct and/or zinc chloride. These compositions are disclosed in Table I and their antimicrobial activity determined using the "Zone of Inhibition Test" determined.

Zone of inhibition test is the relationship between a standard application of a test formulation on a solid agar surface and the resulting zone of inhibited growth of a test organism applied to the agar surface. The larger the zone of growth inhibition, the greater the antimicrobial activity. This test method is used to determine antimicrobial activity in both liquids and solids.

The compositions of Table I which exemplify of the present invention are:

TABLE I

SYNERGISTIC EFFECTS OF $ZnCl_2$ ON THE ACTIVITY OF THE MAGNESIUM SULFATE ADDUCT* vs. PSEUDOMONAS

| | ACTIVE ING.'S AND PERCENTAGE | PHYSICAL FORM | ZONES (mm) vs. PSEUDOMONAS |
|---|---|---|---|
| Example A | Omadine MDS @ 0.135% | Solution | 0 |
| Example B | Aluminum Chlorohydrate (ACH) @ 17.5% | Solution | 0 |
| Example C | Omadine MDS @ 0.135% ACH @ 17.5% | Solution | 0 |
| Example 1 | Omadine MDS @ 0.135% (ACH) @ 17.5% $ZnCl_2$ @ 0.1% | Solution | 7.6 |
| Example D | $ZnCl_2$ @ 0.1% | Lotion | 0 |
| Example E | Omadine MDS @ 0.135% ACH @ 17.5% | Solution | 0 |
| Example 2 | Omadine MDS @ 0.135% ACH @ 17.5% $ZnCl_2$ @ 0.1% | Solution | 8.6 |
| Example F | Omadine MDS @ 0.135% | Solution | 0 |
| Example 3 | Omadine MDS @ 0.135% $ZnCl_2$ @ 0.10% | Solution | 5.6 |
| Example G | $ZnCl_2$ @ 0.10% | Solution | 0 |
| Example | Omadine MDS @ 0.135% | Solution | 0 |

TABLE I-continued

SYNERGISTIC EFFECTS OF ZnCl₂ ON THE ACTIVITY OF THE MAGNESIUM SULFATE ADDUCT* vs. PSEUDOMONAS

| | ACTIVE ING.'S AND PERCENTAGE | PHYSICAL FORM | ZONES (mm) vs. PSEUDOMONAS |
|---|---|---|---|
| Example H | Omadine MDS @ 0.135% ACH @ 17.5% | Solution | 0 |
| Example 4 | Omadine MDS @ 0.135% ACH @ 17.5% ZnCl₂ @ 0.10% | Solution | 8.3 |
| Example J | Base Formula Only | Lotion | 0 |
| Example K | ZnCl₂ 1.0% | Lotion | 2.9 |
| Example L | Omadine MDS 0.225% | Lotion | 1.9 |
| Example 5 | Omadine MDS 0.225% ZnCl₂ 1.0% | Lotion | 11.9 |
| Example M | ZnCl₂ 2.0% | Solution | 1 |
| Example N | Omadine MDS 0.225 | Solution | 0.5 |
| Example 6 | Omadine MDS @ 0.5% ZnCl₂ 2.0% | Powder | 11.3 |

*The magnesium sulfate adduct is sold by Olin Chemicals under the trade name OMADINE MDS.

Another useful determination for evaluating antimicrobial activity is to the minimal inhibitory concentration (M.I.C.) amount. The minimal inhibitory concentration is a serial twofold dilution of the test formulation in a broth culture medium which is innoculated with a standardized culture of microorganisms. The amount of test agent that will inhibit visible microbial growth is termed the minimal inhibitory concentration (M.I.C.) level. The lower the amount of test agent, the greater the antimicrobial activity.

In Table 2 there is reported minimal inhibitory concentration values for Example 7 formed in accordance with the present invention and controls containing only the magnesium sulfate adduct and/or zinc chloride.

TABLE 2

| FORMULA NOS. | ACTIVE ING.'S AND PERCENTAGE | PHYSICAL FORM | MINIMUM INHIBITORY CONCENTRATION (PPM) vs. PSEUDOMONAS |
|---|---|---|---|
| Example O | ZnCl₂ 0.1% | Solution | No Activity |
| Example P | Omadine MDS 0.135% | Solution | 250 |
| Example 7 | Omadine MDS 0.135% ZnCl₂ 0.1% | Solution | 30 |

The results reported in Table 2 indicated no activity for ZnCl₂, activity of 250 ppm for Omadine MDS alone and 30 ppm for the combination of ZnCl₂ with Omadine MDS. This indicates an eightfold increase in activity against *Pseudomonas aeruginosa*.

In still further comparison study compositions were prepared and evaluated both by the minimum inhibitory concentration method and the zone of inhibition. The results were similar for all salts tested at 1% concentration with Omadine MDS at 0.5%. The activities for all the controls were from 125 to 550 ppm using the M.I.C. method and from 4 to 8 ppm for the combination of zinc salt with Omadine MDS. Again, the zone of inhibition was almost non-existent for controls 0–2 mm and 10–14 mm for the combination of the magnesium sulfate adduct and ZnCl₂ combination employed in the present invention.

In Table 3 there is disclosed a surgical scrub composition Composition I employing the anhydrous foaming base composition of pending application Serial No. containing petroleum jelly, mineral oil, glycerine, TiO₂ and sodium cocoyl isethionate and the magnesium sulfate adduct and ZnCl₂ combination of the present invention and the control base Composition II.

TABLE 3

| Formula | Composition I | Composition II |
|---|---|---|
| Petroleum Jelly | 31.00 | 31.00 |
| Mineral Oil | 19.50 | 19.50 |
| Glycerin | 5.00 | 5.00 |
| TiO₂ | 0.50 | 0.50 |
| Na Cocoyl Isethionate | 40.00 | 42.00 |
| Omadine MDS | 2.00 | 2.00 |
| ZnCl₂ (50% Solution) | 2.00 | — |

When tested for antimicrobial activity, the minimum inhibitory concentration activity was enhanced from 125 ppm for the 2% Omadine MDS control Composition II to 2.0 ppm for the Omadine MDS 2%, ZnCl₂ 1% in Composition I. This is over a sixtyfold increase in activity. Evidence for synergism was also observed against *Staphylococcus aureus*, for Composition I activity is 0.003 ppm, while the control Composition II with 2% Omadine is 0.1 ppm. This is a thirty-threefold increase in activity. For *Staphylococcus epidermidis*, once again the synergism was confirmed, with 0.0007 ppm activity for the 2% Omadine MDS 1% ZnCl₂ combination, while the Composition II control is 0.006 ppm. This is an elevenfold increase in activity.

What is claimed is:

1. An antimicrobial composition comprising the magnesium sulfate adduct of 2,2'-dithiobis-pyridine-1,1'-dioxide and a water soluble zinc salt, the zinc salt being in an amount from about 1 to 10 parts by weight per part of the antimicrobial adduct.

2. An antimicrobial composition according to claim 1 wherein the zinc salt is selected from the group consisting of zinc chloride, zinc acetate, zinc sulfate, zinc nitrate and zinc phenylsulfonate.

3. An antimicrobial system according to claim 1 wherein the zinc salt is zinc chloride.

4. An antimicrobial composition according to claim 1, 2 or 3 wherein the zinc salt is in an amount of 1 part by weight per part of the microbial adduct.

5. An antimicrobial composition according to claims 1, 2 or 3 wherein the magnesium sulfate adduct is in an amount from about 0.1 to 1.5% by weight and the zinc salt is in an amount from about 0.1 to 1% by weight of the total composition.

* * * * *